US011353419B2

(12) United States Patent
Liu et al.

(10) Patent No.: US 11,353,419 B2
(45) Date of Patent: Jun. 7, 2022

(54) COMPOSITIONS AND METHODS FOR GAS SAMPLE ANALYSIS

(71) Applicant: Tao Treasures LLC, Frederick, MD (US)

(72) Inventors: Xiaonao Liu, Frederick, MD (US); Yifeng Shi, Hang Zhou (CN)

(73) Assignee: TAO TREASURES, LLC, Frederick, MD (US)

( * ) Notice: Subject to any disclaimer, the term of this patent is extended or adjusted under 35 U.S.C. 154(b) by 305 days.

(21) Appl. No.: 16/422,933

(22) Filed: May 24, 2019

(65) Prior Publication Data
US 2019/0360960 A1    Nov. 28, 2019

Related U.S. Application Data

(60) Provisional application No. 62/677,024, filed on May 27, 2018.

(51) Int. Cl.
| | |
|---|---|
| *G01N 27/407* | (2006.01) |
| *G01N 27/04* | (2006.01) |
| *G01N 33/497* | (2006.01) |
| *G01R 1/067* | (2006.01) |

(52) U.S. Cl.
CPC ......... *G01N 27/4075* (2013.01); *G01N 27/04* (2013.01); *G01N 33/497* (2013.01); *G01N 2033/4975* (2013.01); *G01R 1/06788* (2013.01)

(58) Field of Classification Search
CPC .. G01N 27/04; G01N 27/127; G01N 27/4075; G01N 33/497; G01N 2033/4975; G01R 1/06788
See application file for complete search history.

(56) References Cited

U.S. PATENT DOCUMENTS

| | | | | |
|---|---|---|---|---|
| 5,433,971 A | * | 7/1995 | Royster, Jr. ........... | C07F 11/005 |
| | | | | 427/126.1 |
| 2015/0346190 A1 | * | 12/2015 | Sambandan ......... | G01N 33/497 |
| | | | | 73/23.3 |

OTHER PUBLICATIONS

Dey et al., Dissertation, 2004, 1-117 (Year: 2004).*
Singh et al., ACS Appl. Mater. Interfaces, 2017, 9, 34544-34586 (Year: 2017).*
Jalal et al., ECS Trans. 2017, 1369 (Year: 2017).*
Kaur et al., Sensors and Actuators B, 258, 2018, 1022-1035 (Year: 2018).*
Ohkuwa, Tetsuo et al., "Acetone Response with Exercise Intensity", Advanced Gas Chromatography—Progress in Agricultural, Biomedical and Industrial Applications, pp. 151-160, 2012.
Xing, Ruiqing et al., "Au modified three-dimensional In2O3 inverse opals: synthesis and improved performance for acetone sensing toward diagnosis of diabetes", Nanoscale, vol. 7, No. 30, pp. 1-9, Aug. 14, 2015.

(Continued)

*Primary Examiner* — Gurpreet Kaur
(74) *Attorney, Agent, or Firm* — Novick, Kim & Lee, PLLC; Allen Xue

(57) ABSTRACT

A method of detecting acetone in a gas sample, comprising, at an operation temperature of 50° C. or less, exposing the gas sample to a gas sensor comprising an electrode and a sensing material deposited on the electrode, wherein the sensing material comprises tungsten bronze, and a level of the acetone in the gas sample is detected by a change in resistivity of the sensing material.

11 Claims, 14 Drawing Sheets

(a) 
Interdigitated Au electrode (b) 
Spin coating deposition (c) 
Drying

(56) References Cited

OTHER PUBLICATIONS

King, Julian et al., "Measurement of endogenous acetone and isoprene in exhaled breath during sleep", Physiological Measurement, vol. 33, pp. 413-428, 2012.
Zhou, Xin et al., "Nanosheet-Assembled ZnFe2O4 Hollow Microspheres for High-Sensitive Acetone Sensor", Applied Materials & Interfaces, pp. A-H, Accepted: Jun. 23, 2015.
Choi, Seon-Jin et al., "Selective Detection of Acetone and Hydrogen Sulfide for the Diagnosis of Diabetes and Halitosis Using SnO2 Nanofibers Functionalized with Reduced Graphene Oxide Nanosheets", Applied Materials & Interfaces, pp. 2588-2597, Published: Jan. 23, 2014.
Choi, Seon-Jin et al., "Selective Diagnosis of Diabetes Using Pt-Functionalized WO3 Hemitube Networks as a Sensing Layer of Acetone in Exhaled Breath", Analytical Chemistry, pp. 1792-1796, Published: Dec. 20, 2012.
Righettoni, Marco et al., "Si:WO3 Sensors for Highly Selective Detection of Acetone for Easy Diagnosis of Diabetes by Breath Analysis", Analytical Chemistry, vol. 82, No. 9, pp. 3581-3587, May 1, 2010.
Yang, Chia-Ming et al., "Ultraviolet illumination effect on monolayer graphene-based resistivVe sensor for acetone detection", Vacume, vol. 140, pp. 89-95, Jun. 2017.
Staerz, Anna et al., "Understanding the Potential of WO3 Based Sensors for Breath Analysis", Sensors, vol. 16, No. 1815, Published: Oct. 29, 2016.
Kim, Do Hong et al., "Vertically Ordered Hematite Nanotube Array as anUltrasensitive and Rapid Response Acetone Sensor", Applied Materials & Interfaces, pp. 1-21, Published (Web): Aug. 26, 2014.

\* cited by examiner

COMPOSITIONS AND METHODS FOR GAS SAMPLE ANALYSIS

CROSS-REFERENCE TO RELATED APPLICATIONS

This application claims the benefit of U.S. Provisional Application No. 62/677,024, filed May 27, 2018. The entire contents of the above-identified applications are hereby fully incorporated herein by reference.

TECHNICAL FIELD

The subject matter disclosed herein is generally directed to compositions, materials, gas sensors, devices, and methods for analyzing gas samples.

BACKGROUND

Volatile organic compounds (VOCs) released from human body contain information that can be used as indicators of health status (e.g., metabolic profiles) of the individual. Monitoring VOCs has been used to detect and investigate health status and diseases. The improvement in monitoring, analyzing, and correlating the VOCs to the health information can lead to development of new healthcare and medical devices with an unprecedented market.

Acetone is one of the most abundant components in VOCs released from the skin and in breath that related to metabolic disorders. Acetone may be an indicator of blood glucose levels (e.g., in diabetes testing), fat burning, and prolonged fasting and ketogenic diet. The concentration of acetone released from the breath and the skin of healthy individuals can be from 100 parts per billion (ppb) to 10 parts per million (ppm). Current gas sensing materials for acetone detection suffers from limitations such as high operation temperature, complexity in fabrication, and poor chemical stability in the air. For example, some of the materials can be easily oxidized in the air when heated, exposed to UV light or visible light, or exposed to moistures with oxygen. Sensors based on current sensing materials have to operate at a high temperature, ranging from 160° C. to 475° C., which limit the application in detecting samples at room temperature and lead to high power consumption. This can limit the application of these sensors in real-time environment monitoring, wearables, and medical devices. Therefore, there is a need for gas sensors and sensing materials that are stable and capable of detecting ppm and ppb levels of acetone at room temperature.

SUMMARY

In one aspect, the present disclosure includes a method of detecting acetone in a gas sample, comprising, at an operation temperature of 50° C. or less, exposing the gas sample to a gas sensor comprising an electrode and a sensing material deposited on the electrode, wherein the sensing material comprises tungsten bronze, and a level of the acetone in the gas sample is detected by a change in resistivity of the sensing material.

In some embodiments, the operation temperature is 30° C. or less, 25° C. or less, or 20° C. or less. In some embodiments, concentration of acetone in the gas sample is 100 parts per million (ppm) or less, 10 ppm or less, 1 ppm or less, or 100 parts per billion (ppb) or less. In some embodiments, the gas sample is a breath sample or comprises a vapor released from a skin of a subject. In some embodiments, the tungsten bronze comprises $M_xWO_y$, and M is an alkali metal element. In some embodiments, wherein the sensing material comprises $Na_{0.15}WO_3$, $Cs_{0.33}WO_3$, $Na_{0.12}K_{0.2}WO_3$, carbon-$M_xWO_y$ complex, or a combination thereof. In some embodiments, the x is 0.5 or less and the y is in a range from 2 to 3. In some embodiments, the tungsten bronze comprises $M_xM'_{x'}WO_y$, y, and M is a first alkali metal element and M' is a second alkali metal element. In some embodiments, the sensing material comprises a complex of carbon and the tungsten bronze. In some embodiments, the sensing material comprises a complex of reduced graphene oxide and the tungsten bronze, or a complex of graphene oxide and tungsten bronze. In some embodiments, the sensing material comprises reduced graphene oxide-$Na_{0.1}WO_3$. In some embodiments, the skin is skin of a palm, finger, ear, nose, face, eye, arm, leg, chest, breast, back, abdomen, or foot of the subject.

In another aspect, the present disclosure includes a gas sensor comprising: an electrode and a sensing material deposited on the electrode, wherein the sensing material comprises tungsten bronze, and the gas sensor has a limit of detection of 100 parts per million (ppm) or less of acetone in a gas sample at an operation temperature of 50° C. or less.

In some embodiments, the limit of detection is 50 ppm or less, 10 ppm or less, 1 ppm or less, or 100 parts per billion (ppb) or less. In some embodiments, the tungsten bronze is $M_xWO_y$, and M is an alkali metal element. In some embodiments, the tungsten bronze is $M_xM'_{x'}WO_y$, and M is a first alkali metal element and M' is a second alkali metal element. In some embodiments, the sensing material comprises a complex of carbon and the tungsten bronze. In some embodiments, the electrode substrate comprises ceramic, silica, silicon, glass, printed circuit board (PCB), or polyethylene terephthalate (PET) substrate. In some embodiments, the gas sensor further comprises a depositing solvent, an adhesive, or both. In some embodiments, the sensing material is in a shape of a film.

In another aspect, the present disclosure includes a wearable device comprising the gas sensor herein. In some embodiments, the wearable device has a volume of 5 $cm^3$ or less. In some embodiments, the wearable device has a power consumption of 5 μAmp or less. In some embodiments, wherein the wearable device comprises a shoe, an armband, a sleeve, a jacket, glasses, eye wears, goggles, a glove, a ring, a watch, a wristband, a bracelet, nose ring, ear bud, earphone, an article of clothing, a hat, a headband, a headset, a bra, or jewelry. In some embodiments, the wearable device is configured to calibrate itself and/or to digitally read concentration of acetone. In some embodiments, the wearable device is configured to connect with a computer or smartphone that visualizes metabolic profiles, fat burning status, diet and fitness efficiency, or a combination thereof, in a subject wearing the wearable device.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
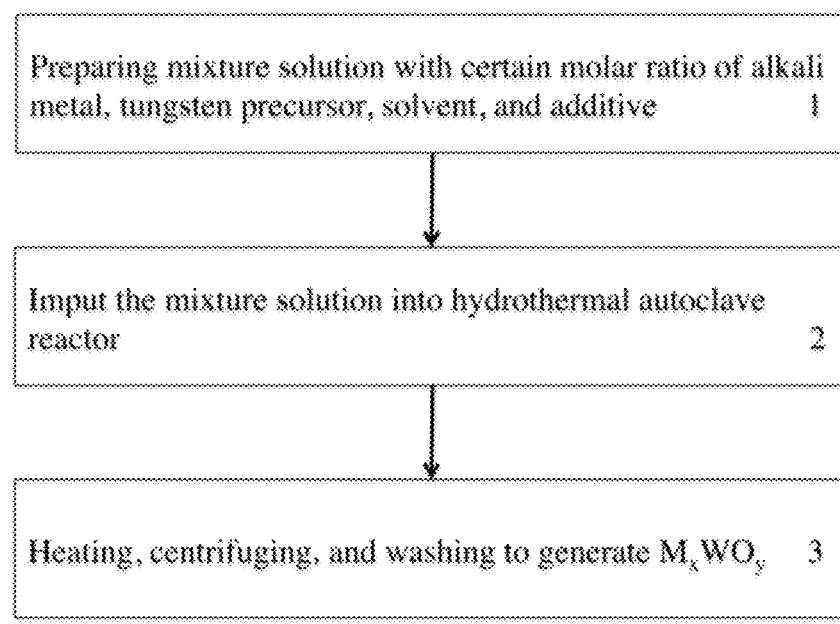
FIG. 1 shows a flow chart of an example method for preparing a gas sensing material according to some embodiments.

The figures herein are for illustrative purposes only and are not necessarily drawn to scale.

DETAILED DESCRIPTION OF THE EXAMPLE EMBODIMENTS

General Definitions

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides for compositions, materials, gas sensors, devices, and methods for detecting one or more components (e.g., acetone) in a gas sample released from a subject, e.g., in the breath, or VOCs or vapor emitted from the skin or other parts of the body. In certain examples, the detecting includes detecting the concentration of the one or more components (e.g., acetone). In an aspect, the present disclosure provides highly sensitive sensors for detecting and measuring acetone in a gas sample. In certain cases, such sensors are capable of detecting ppm and ppb concentration of acetone at a relatively low operation temperature (e.g., room temperature).

In some embodiments, the compositions or materials herein may be semiconductors whose conductivity and/or resistivity alters in response to the presence of low concentration of biomarker(s) of metabolism profiles (e.g., blood sugar, body fat burning, diabetes, etc.). In some embodiments, the biomarker is acetone, e.g., acetone emitted from the skin of a subject.

In an aspect, the present disclosure provides for a gas sensor for detecting low concentration (e.g., in the range of ppm or ppb) of acetone at room temperature. In general, the gas sensor may comprise sensing materials comprising tungsten bronze ($M_xWO_y$, where M may be an alkali metal element) and/or carbon-tungsten bronze nanocomposite. Such compositions, materials, gas sensor, and devices may allow for energy efficient, inexpensive, rugged, user-friendly, and non-invasive detection of metabolic profiles. The methods, compositions, materials, gas sensors, and devices herein may be used for detecting and measuring fresh and native VOCs released from the skin of a subject, e.g., skin of palm, finger, ear, nose, face, eye, arm, leg, chest, breast, back, abdomen, and/or or foot, thus allowing real-time monitoring the dynamic change of emitted VOCs from the subject.

Gas Sensors

Provided herein include gas sensors. The gas sensors may be used for detecting one or more components in a gas sample. In some embodiments, the component(s) is a biomarker. In certain examples, the biomarker is acetone. The gas sensor may comprise a sensing material. In some examples, the gas sensor comprises: an electrode and a sensing material deposited on the electrode, wherein the sensing material comprises tungsten bronze, and the gas sensor has a limit of detection of 100 parts per million (ppm) or less of acetone in an gas sample at an operation temperature of 50° C. or less. In some examples, the methods, compositions, materials, gas sensors, and devices herein may detect from about 100 ppb to about 100 ppm of acetone in a sample.

In some embodiments, the sensing material comprises tungsten bronze. In some embodiments, tungsten bronze is a compound with a formula $M_xWO_y$, where M is a alkali metal element (e.g., ion). Tungsten bronze materials may have bright colors and the color of these compounds varies with the content of the alkali metal, from golden-yellow to blue-violet. In some cases, the alkali metal ions do not replace tungsten atom in the crystal structure of tungsten bronze. Rather, the alkali metal ions may exist in the pore space formed in the crystal frameworks composed by tungsten and oxygen. Examples of tungsten bronze are described in *The tungsten bronzes and related compounds*. Quarterly Reviews, Chemical Society, 1968, 22(1): 30-44. The sensing materials herein may comprise one type of tungsten bronze. Alternatively or additionally, the sensing material herein may comprise two or more, e.g., 2, 3, 4, 5, or more types of tungsten bronze compounds.

The alkali metal element (e.g., ion) in the tungsten bronze may be any element in Group IA in the periodic table. Examples of alkali metal elements include lithium, sodium, potassium, rubidium, cesium, and francium. For examples, the tungsten bronze may be $Li_xWO_y$, $Na_xWO_y$, $K_xWO_y$, $Rb_xWO_y$, $CsWO_y$, or $Fr_xWO_y$. In some cases, the tungsten bronze comprises two or more kinds of alkali metal elements. For example, the tungsten bronze may comprise 2, 3, 4, 5, or more alkali mental elements. In some cases, the tungsten bronze comprises 2 alkali mental elements and has a formula of $M_xM'_{x'}WO_y$. Examples of such tungsten bronze include $Li_xNa_{x'}WO_y$, $Li_xK_{x'}WO_y$, $Li_xCs_{x'}WO_y$, $Na_xK_{x'}WO_y$, $Na_xCs_{x'}WO_y$, and $K_xCs_{x'}WO_y$.

The tungsten bronze in the sensing materials may have values x and y in the formula $M_xWO_y$ that make the material suitable for gas sensing. In some cases, the x value may be from 0.01 to 1. In certain examples, the x value may be 0.5 or less. For example, the x value may be 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.50. In cases where the tungsten bronze has a formula of $M_xM'_{x'}WO_y$, the x value may be from 0.01 to 1; and the x' value may be from 0.01 to 1. In certain cases, the x value may be 0.5 or less and the x' value may be 0.5 or less. For example, the x value may be 0.5 or less, e.g., 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.50; and the x' value may be 0.5 or less, e.g., 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.50. In some cases, the y value may be from 2 to 3, e.g., 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, or 3. In a particular example, y is 3. Examples of tungsten bronze include $Na_{0.15}WO_3$, $Cs_{0.33}WO_3$, and $Na_{0.12}K_{0.2}WO_3$.

In some embodiments, the sensing material comprises a carbon-tungsten bronze complex. In some cases, the carbon-tungsten bronze complex comprises one or more tungsten bronze compounds and one or more types of carbon. The carbon in the complex may be carbon blacks, carbon nanotube, carbon nanofiber, carbon nanospheres, carbon nanosheet, carbon nanowire, carbon nanorod, graphene, graphene oxide, reduced graphene oxide, graphite oxide, or any combination thereof. In some examples, the carbon may be graphene oxide. In certain examples, the carbon may be reduced graphene oxide. Graphite oxide may be a solid with C:O ratio between 2 and 3 (e.g., obtained by treating graphite with strong oxidizers). Graphite oxide can be dispersed by sonication in polar solvents to yield monomolecular sheets, known as graphene oxide. Graphene oxide may be an oxide formed by oxidizing graphite which includes graphite oxide. The graphene oxide includes an oxygen-containing functional group, such as a hydroxyl group, an epoxide group, a carboxyl group, a ketone group, a lactone group, an aldehyde group, an ester group, a carbonate group, a peroxide group, an ether group, an acetal group, an acetal group, or the like, or a combination thereof, e.g., in a carbon layer, and thus a distance between stacked layers of the graphene oxide is increased so that the distance between the stacked layers of the graphene oxide is sufficient for gas molecules to permeate. Reduced graphene oxide may be a reduced substance that is obtained by reducing graphene oxide. In some cases, reduced graphene oxide may not include a graphene of a complete form (e.g., having a C=C/C—C fully conjugated structure) but includes a fewer number of C=C bonds than graphene and may comprise oxygen atoms and/or nitrogen atoms amongst the carbon atoms.

Graphene oxide may contain one or more oxygen functional groups. By reducing graphene oxide, these oxygen functional groups may be removed, to obtain a graphene-like material, which is called as reduced graphene oxide. In certain examples, the carbon may be reduced graphene oxide (rGO).

The carbon-tungsten bronze may be complexes (e.g., nanocomposites) of reduced graphene oxide (rGO) and tungsten bronze, complexes of graphene oxide and any tungsten bronze, or any combination thereof. In some examples, the carbon-tungsten bronze is carbon-$M_xWO_y$. In certain examples, the carbon-tungsten bronze may be (rGO)-$M_xWO_3$, e.g., (rGO)—$Na_{0.1}WO_3$.

The sensing material may be in a suitable shape for functioning in a gas sensor. For example, the sensing material may be a film, e.g., with a thickness of from 50 nm to 300 nm.

The sensing material herein may be in the form of nanomaterial. Examples of nanomaterials include nanowire, nanorod, nanosphere, nanoporous, nanoplate, nanosheet, nanomesh, nanotube, and nanoscroll.

In some embodiments, the gas sensors may further comprise one or more electrodes. The electrodes may measure the change in resistivity, resistance, and/or conductivity of the sensing material (e.g., when the sensing material is exposed to a gas sample) deposited on the electrodes. Examples of electrodes include those made from platinum (Pt), gold (Au), palladium (Pd), iridium (Ir), silver (Ag), ruthenium (Ru), nickel (Ni), stainless steel (STS), copper (Cu), titanium (Ti), tungsten (W), and a combination thereof.

The electrode(s) may be deposited on one or more electrode substrates. Examples of the electrode substrates include aluminum (Al), molybdenum (Mo), chromium (Cr), ceramic substrate, alumina ($Al_2O_3$) substrate, silicon (Si) substrate, glass, printed circuit board (PCB), polyethylene terephthalate (PET) flexible substrate, and silicon oxide ($SiO_2$) substrate. In certain examples, the electrode substrate is ceramic substrate. In some examples, the gas sensors comprise interdigitated electrode(s), which comprise one or more electrodes deposited on one or more substrates.

The sensing materials may be deposited on the electrodes. The deposition may be achieved using one or more depositing solvents. Examples of the depositing solvents include water, acetone, methanol, ethanol, propanol, butanol, ethylene glycol, propylene glycol, glycerol, benzyl alcohol, or any combination thereof. Alternatively or additionally, the sensing materials may be deposited on the electrodes with one or more adhesives. Examples of the adhesives include polyvinyl alcohol (PVA), Polytetrafluoroethylene (PTFE), Carboxymethyl Cellulose (CMC), polyvinylidene difluoride (PVDF), Polyacrylonitrile (PAN), or any combination thereof. The deposition may be performed by spin coating, printing (e.g., 2-D printing, 3-D printing, etc.), or drop coating.

Devices

The present disclosure further provides devices comprising one or more of the gas sensors described herein. In certain embodiments, the devices further comprise a power supply, display, a computer, a microcontroller unit, a read-out circuit, a communication module (e.g., a wireless communication module), a memory, or any combination thereof.

The devices may be incorporated in (e.g., as a part of) and/or interoperable with an interactive mobile devices or applications with Internet of Things (IoT) features. In some examples, the devices may be integrated to or a part of professional training devices, athlete training devices, smart phones, wearable devices, health care devices, medical devices, fitness equipment (e.g., treadmill, elliptical, etc.), or a combination thereof. The device may detect VOCs, e.g., those from breath or emitted from the skin (e.g., the skin of, the palm, finger, ear, nose, face, eye, arm, leg, chest, breast, back, abdomen, or foot of a subject).

The devices may be wearable devices. In some cases, with the sensing materials herein, a gas sensor array sensitive to the emitted VOCs may be fabricated as a wearable device by deposition. Examples of wearable devices include a shoe, an armband, a sleeve, a jacket, glasses, eye wears, goggles, a glove, a ring, a watch, a wristband, a bracelet, nose ring, ear bud, earphone, an article of clothing, a hat, a headband, a headset, a bra, and jewelry.

The devices may be portable devices. In some cases, with the sensing materials herein, a gas sensor array sensitive to the emitted VOCs may be fabricated as a portable device by deposition. Examples of portable devices include a keychain and a Breathalyzer.

The devices herein may be functional with relatively low power consumption. For example, the devices may have a power consumption of at most 20 μAmp, at most 10 μAmp, at most 9 μAmp, at most 8 μAmp, at most 7 μAmp, at most 6 μAmp, at most 5 μAmp, at most 4 μAmp, at most 3 μAmp, at most 2 μAmp, or at most 1 μAmp.

The devices may be relatively small in size. For example, the device may have a volume of at most 30 $cm^3$, at most 20 $cm^3$, at most 15 $cm^3$, at most 10 $cm^3$, at most 8 $cm^3$, at most 6 $cm^3$, at most 5 $cm^3$, at most 4 $cm^3$, at most 3 $cm^3$, at most 2 $cm^3$, or at most 1 $cm^3$.

In some cases, the devices are intelligent. For example, the devices may be configured to calibrate (e.g., self-calibrate). The calibration may be performed based on reference information specific for an individual user.

The devices may be configured to digitally read VOCs (e.g., acetone) concentrations. The devices may convert signals from one form to another. For example, the devices may convert analog signals into digital signals, and/or convert digital signals into measurements of energy consumption and/or metabolic profiles of the user subject.

The devices may transfer data wirelessly, e.g., via internet, Bluetooth, Bluetooth low energy (BLE), or a combination thereof. The devices may be configured to connect with smartphones or computers (e.g., laptops) to visualize, monitor, analyze metabolic profiles and statuses, fat burning status, diet and fitness efficiency, or a combination thereof of a subject using (e.g., wearing) the devices.

Methods of Detection

Further provided herein are methods for detecting one or more analytes (e.g., acetone) in a gas sample. In some embodiments, the methods comprise exposing a gas sample to the gas sensor described herein. When exposed to one or more analytes in the gas sample, the resistivity of the sensing material may change. The change may be measured and/or monitored as an indicator of the level of the one or more analytes in the gas sample. In some examples, the analyte is acetone. In some example, the method of detecting acetone in a gas sample, comprising, at an operation temperature of 50° C. or less, exposing the gas sample to a gas sensor comprising an electrode and a sensing material deposited on the electrode, wherein the sensing material comprises tungsten bronze, and a level of the acetone in the gas sample is detected by a change in resistivity of the sensing material.

The methods herein may comprise exposing the gas sensor to a gas sample. As used herein, a gas sample refers to any samples comprising one or more gaseous components. A gas sample may further comprise aqueous components (e.g., fog) or solid components (e.g., smoke). A gas sample may be a breath sample. A gas sample may comprise VOCs or vapor from a subject, e.g., from the skin or breath of a subject. In some cases, the VOCs (e.g., acetone) or vapor is emitted from the skin of a subject. The skin may be that of any part of the subject, e.g., the palm, finger, arm, leg, back, abdomen, or foot of the subject. In some examples, the gas sample comprises acetone.

The methods may be performed at a relatively low operation temperature. In some embodiments, the operation temperature may be at most 100° C., at most 80° C., at most 60° C., at most 50° C., at most 40° C., at most 30° C., at most 20° C., or at most 10° C. In some examples, the operation temperature may be in a range from about −30° C. to about 40° C., e.g., from about 0° C. to 30° C., from about 10° C. to about 30° C., or from about 20° C. to about 25° C. In some examples, the operation temperature may be 50° C. or less.

The methods, gas sensors, and devices herein may detect relatively low levels of analytes (e.g., acetone). In some cases, the methods and devices may detect acetone at a concentration of 1000 parts per million (ppm) or less, e.g., 500 ppm or less, 100 ppm or less, 50 ppm or less, 10 ppm or less, 1 ppm or less, 800 parts per billion (ppb) or less, 600 ppb or less, 400 ppb or less, 200 ppb or less, 100 ppb or less, 80 ppb or less, 60 ppb or less, 40 ppb or less, 20 ppb or less, 10 ppb or less, or 1 ppb or less, of acetone. In some cases, the methods, sensors, and devices may be configured to have a limit of detection of 500 parts per million (ppm) or less of analyte (e.g., acetone). By "limit of detection" is meant the lowest quantity of a substance that can be distinguished from the absence of that substance (e.g., a blank value). In certain cases, the gas sensor or device are configured to have a limit of detection of 500 ppm or less, such as 400 ppm or less, including 300 ppm or less, 200 ppm or less, 100 ppm or less, 75 ppm or less, 50 ppm or less, 25 ppm or less, 20 ppm or less, 15 ppm or less, 10 ppm or less, 5 ppm or less, 1 ppm or less, 500 ppb or less, 100 ppb or less, 50 ppb or less, 10 ppb or less, or 1 ppb or less. In certain cases, the gas sensor or device is configured to have a limit of detection of 1 ppm or less. In certain cases, the gas sensor or devices is configured to detect at least 1 ppb, at least 10 ppb, at least 50 ppb, at least 100 ppb, at least 500 ppb, at least 1 ppm, at least 5 ppm, at least 10 ppm, at least 15, ppm, at least 20 ppm, at least 25 ppm, at least 50 ppm, at least 75 ppm, at least 100 ppm, or at least 200 ppm of the VOCs (e.g., acetone).

Methods of Making

FIG. 1 shows an example method for preparing a sensing material described herein. $M_xWO_y$ composite may be synthesized by using a facile hydrothermal treatment of mixture precursor solutions comprising a tungsten precursor, an alkali metal (e.g., ion) precursor, solvents, and additives. The tungsten precursor, the alkali metal (e.g., ion) precursor, and additives may be added into the solvent to form a precursor mixture. And then, the mixture may be transferred into a hydrothermal autoclave reactor and heated at a temperature between 140° C.~260° C. for 4 hours~72 hours. When the reactor cooled down to room temperature, the tungsten bronze material may be obtained by centrifugation and washing.

The tungsten precursor may be prepared using one or more (e.g., a mixture) of $WCl_6$, $WCl_5$, $WOCl_4$, and $WO_2Cl_2$. The alkali metal (e.g., ion) precursor may be prepared using one or more (e.g., a mixture) of alkali metal salts and hydroxides, e.g., LiCl, NaCl, KCl, CsCl, $Li_2CO_3$, $Na_2CO_3$, $K_2CO_3$, $Cs_2CO_3$, $Li_2SO_4$, $Na_2SO_4$, $K_2SO_4$, $Cs_2SO_4$, LiOH, NaOH, KOH, CsOH, $CH_3COOLi$, $CH_3COONa$, $CH_3COOK$, $CH_3COOCs$, and hydrates thereof. The solvent may comprise one or more (e.g., a mixture) of alcohols, e.g., methanol, ethanol, propanol, butanol, ethylene glycol, propylene glycol, glycerol, and benzyl alcohol. Additives may be added into the solvent (e.g., to improve the synthesis). The additives may comprise one or more (e.g., a mixture) of water, formic acid, acetic acid, propionic acid, butyric acid, oxalic acid, glycolic acid, citric acid, ascorbic acid, and malic acid.

The mixture solution may be made using suitable molar ratio among tungsten precursor(s), alkali metal (e.g., ion) precursor(s), solvent(s), and additive(s). Examples of molar ratio is shown in Table 1 below:

TABLE 1

| Molar ratio | 0~1 | 0.01~0.8 | 0.1~500 | 0~10 |
|---|---|---|---|---|
| Components | Tungsten precursor | alkali metal (e.g., ion) precursor | solvent | additives |

The pure $M_xWO_y$ composite may be obtained by centrifugation and washing with solvent. The washing solvent comprise one or more of water, acetone and alcohols, including water, acetone, methanol, ethanol, propanol, and butanol.

Figure 2:
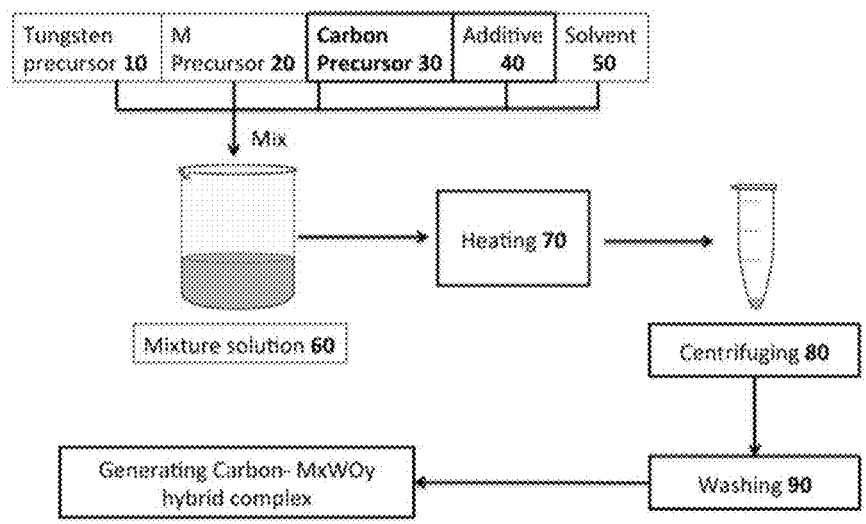
FIG. 2 shows an example schematic diagram for generating carbon-$M_xWO_y$ complex according to some embodiments.

FIG. 2 shows another example method of preparing sensing materials herein. Carbon-$M_xWO_y$ complex may be synthesized using a facile hydrothermal treatment of mixture precursor solutions comprises a tungsten precursor, a carbon precursor, an alkali metal (e.g., ion) precursor, solvents and additives. The tungsten precursor, the carbon precursor, the alkali metal (e.g., ion) precursor, and the additives may be added into a solvent to form a precursor mixture. And then, the mixture may be transferred into a hydrothermal autoclave reactor and heated at a temperature between 140° C.~260° C. for 4~72 hours. When the reactor cools down to room temperature, the Carbon-$M_xWO_y$ complex may be obtained by centrifugation and washing.

The carbon precursor may comprise carbon blacks, carbon nanotubes, carbon nanofibers, carbon nanospheres, carbon nanosheet, carbon nanowire, carbon nanorod, graphene, graphene oxide, reduced graphene oxide, or any combination thereof. The tungsten precursor may be prepared using one or more (e.g., a mixture) of $WCl_6$, $WCl_5$, $WOCl_4$, $WO_2Cl_2$. The alkali metal (e.g., ion) precursor may be prepared using one or more (e.g., a mixture) of alkali metal salts and hydroxides, e.g., LiCl, NaCl, KCl, CsCl, $Li_2CO_3$, $Na_2CO_3$, $K_2CO_3$, $Cs_2CO_3$, $Li_2SO_4$, $Na_2SO_4$, $K_2SO_4$, $Cs_2SO_4$, LiOH, NaOH, KOH, CsOH, $CH_3COOLi$, $CH_3COONa$, $CH_3COOK$, $CH_3COOCs$, and hydrates thereof. The solvent may be one or more (e.g., a mixture) of alcohols, e.g., methanol, ethanol, propanol, butanol, ethylene glycol, propylene glycol, glycerol, and benzyl alcohol. The additives may be added into the solvent (e.g., to improve the synthesis). The additives may be one or more (e.g., a mixture) of water, formic acid, acetic acid, propionic acid, butyric acid, oxalic acid, glycolic acid, citric acid, ascorbic acid, and malic acid.

The mixture solution may be made using the suitable molar ratio among tungsten precursor(s), alkali metal (e.g., ion) precursor(s), solvent(s), and additive(s). Examples of molar ratio is shown in Table 2 below:

TABLE 2

| Molar ratio | 0~1 | 0~1 | 0.01~0.8 | 0.1~500 | 0~10 |
|---|---|---|---|---|---|
| Components | Tungsten precursor | Carbon precursor | alkali meta (e.g., ion) precursor | solvent | additives |

Figure 14:
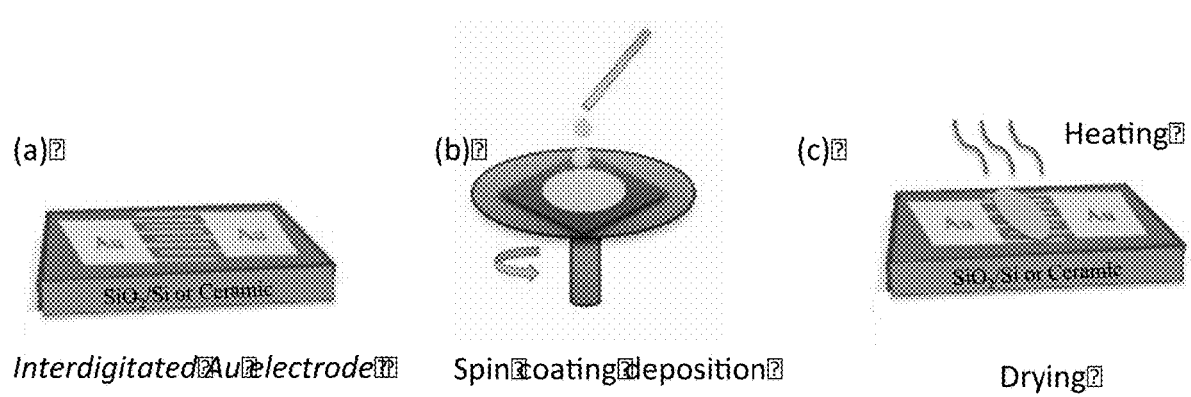
FIG. 14 shows an exemplary method for making rGO-$M_xWO_3$.

In an example method for fabrication of rGO-$M_xWO_3$ gas sensors, interdigitated electrodes (e.g., Au) with 100 nm thicknesses may be deposited on a $SiO_2$/Si substrate or ceramic substrate. The prepared optimized concentration of rGO-$M_xWO_3$ solution may then be spin-coated over the interdigitated electrode with the optimized amount. There may be an interdigital gap between the electrodes. The interdigital gap of the electrodes may be from 10 μm to 50 μm. Then the nanocomposite gas sensor may be dried for from 0.5 hour to several hours (e.g., 0.5 to 1 hour) in a heater (e.g., furnace) at 20-100° C. or under a UV light in air or nitrogen atmosphere. An exemplary method is shown in FIG. 14.

Another example method for fabrication of the rGO-$M_xWO_3$ gas sensor is outlined below. First, 30-50 mg of the rGO-$M_xWO_3$ nanocomposites may be ultrasonically dispersed in 0.1-5 mL of distilled water or ethanol for 30 minutes-5 hours to form a suspension. The suspension may then be dropped onto an interdigitated electrode (e.g., Au or Pt electrode). The chip may then be placed in air for several minutes allowing the diffusion of suspension through the whole surface of electrode, which is then dried in ambient air at 25-100° C. (e.g. 35° C.). The thickness of rGO-$M_xWO_3$ layer may be adjusted by repeating the above procedures.

EXAMPLES

Example 1

This example shows example methods for synthesis of (rGO)—$Na_{0.1}WO_3$ and the application for acetone detection at room temperature.

Preparation of reduced graphene oxide (rGO)—$Na_{0.1}WO_3$ complex e is outlined below. The rGO-$Na_{0.1}WO_3$ complex was synthesized using a facile hydrothermal treatment of $WCl_6$ solution in the presence of graphene oxide (GO). In an example synthesis process, 40 mg $WCl_6$, 1.5 mg $Na_2CO_3$ and 1 mg GO were added into 25 mL of ethanol with ultrasonication for 1 h. And then, the dispersion was transferred into a 50 mL hydrothermal autoclave reactor and was heated at 180° C. for 12 h. Afterward, when the autoclave reactor cooled down to room temperature, the products were obtained by centrifugation at 3000 r/min for 15 min, and subsequent washing with deionized water for several times.

The rGO-$Na_{0.1}WO_3$ nanocomposite sensor was fabricated on a ceramic electrode substrate. A pair of the Au electrode had a thickness of 150 nm. The width and gap of the electrode pair were 20 μm and 10 μm, respectively. The sensing film of rGO-$Na_{0.1}WO_3$ nanocomposite was prepared using drop-casting method. The resulting rGO-$Na_{0.1}WO_3$ dispersion was dropped onto the ceramic electrode substrate with a pipette, followed by drying in the oven at 30° C. for 5 hours to generate acetone sensor.

Figure 3:
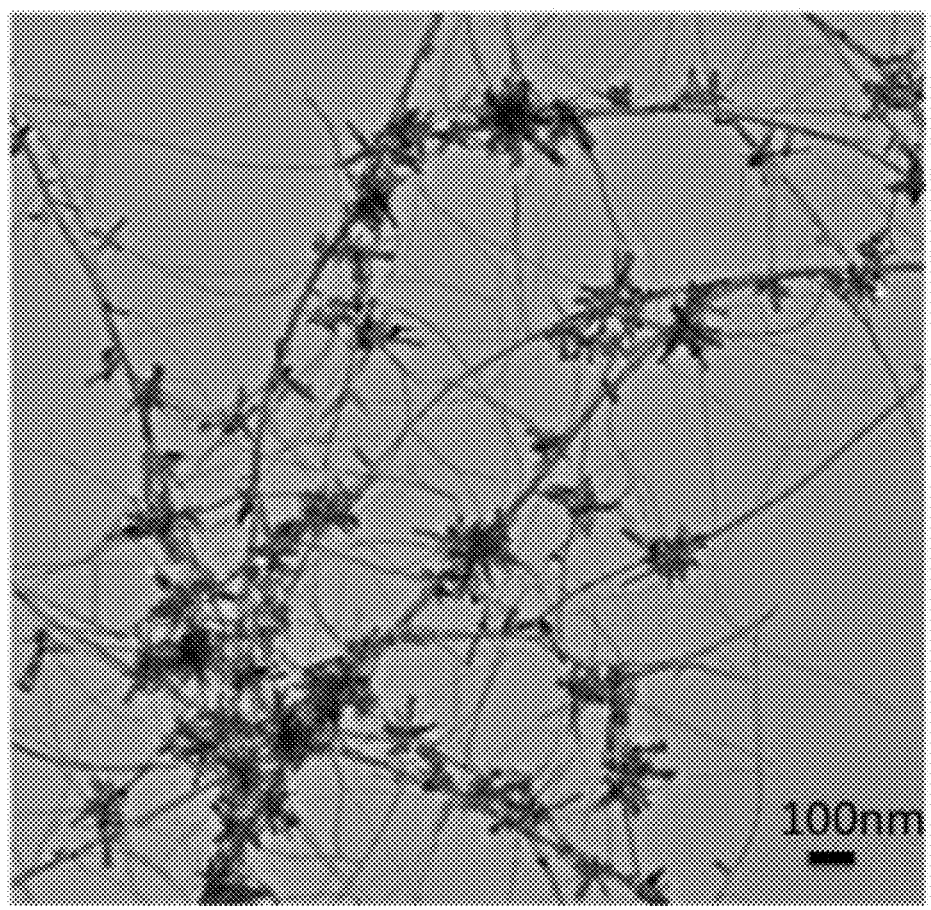
FIG. 3 shows a TEM image of rGO-$Na_{0.1}WO_3$ complex.

The particle morphology of rGO-$Na_{0.1}WO_3$ complex was displayed by Transmission Electron Microscope (TEM) in FIG. 3. The elemental ratio (Na:W) was determined by X-Ray Fluorescence Spectroscopy (XRF).

Figure 4:
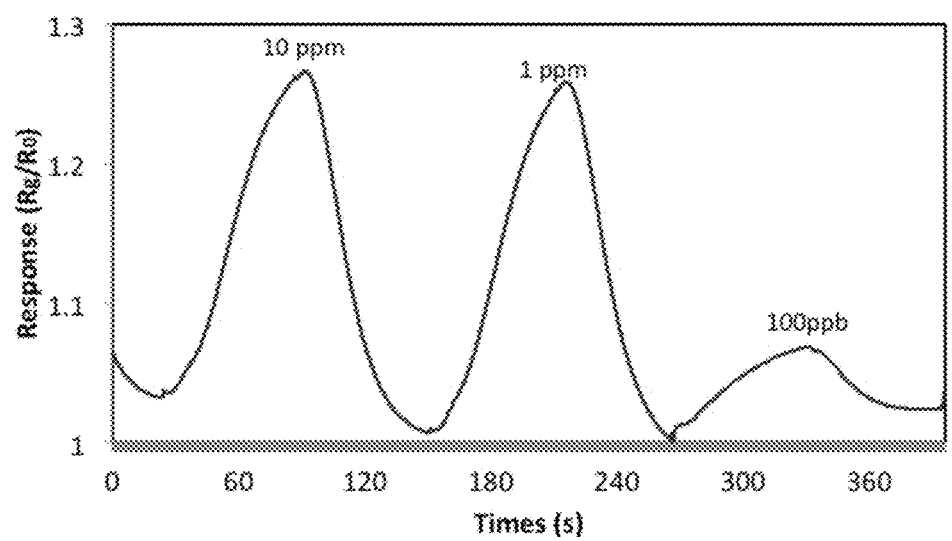
FIG. 4 shows the response curves of the rGO-$Na_{0.1}WO_3$ film sensor measured under various acetone gas concentrations at room temperature.

The response of the sensor was defined as $S=R_g/R_0$, where $R_0$ was the resistance of sensors in air. Rg was the resistance in the presence of the acetone gas. The measurement was performed at room temperature with acetone gas exposure concentration ranging from 100 ppb to 10 ppm, and the test was switched from low concentration to high concentration. A clear increase in the sensor response of rGO-$Na_{0.1}WO_3$ was observed with the increasing of gas concentration, as shown in FIG. 4.

Example 2

This example shows example synthesis methods of $Na_{0.15}WO_3$ and the application for acetone detection at room temperature.

$Na_{0.15}WO_3$ was synthesized using a facile hydrothermal treatment of $WCl_6$ solution. In an example synthesis process, 40 mg $WCl_6$ and 1.2 mg sodium acetate were added into 25 mL of ethanol with ultrasonication for 5 min. And then, the dispersion was transferred into a 50 mL hydrothermal autoclave reactor and was heated at 200° C. for 48 h. Afterward, when the autoclave reactor cooled down to room temperature, the products were obtained by centrifugation at 3000 r/min for 15 min. The pure $Na_{0.15}WO_3$ powders were finally obtained after being washed with water and ethanol three times respectively and dried at 50° C. overnight. The sodium tungsten bronze ($Na_{0.15}WO_3$) powders (2 mg) were prepared in the 10 μl ethanol solution to form $Na_{0.15}WO_3$ dispersion for sensor making.

The $Na_{0.15}WO_3$ sensor was fabricated on a ceramic electrode substrate. A pair of the Au electrode had a thickness of 150 nm. The width and gap were 20 μm and 10 μm, respectively. The sensing film of $Na_{0.15}WO_3$ was prepared by using drop-casting method. The resulting $Na_{0.15}WO_3$ dispersion was dropped onto the ceramic electrode substrate with a pipette, followed by drying in the oven at 30° C. for 5 h.

Figure 5:
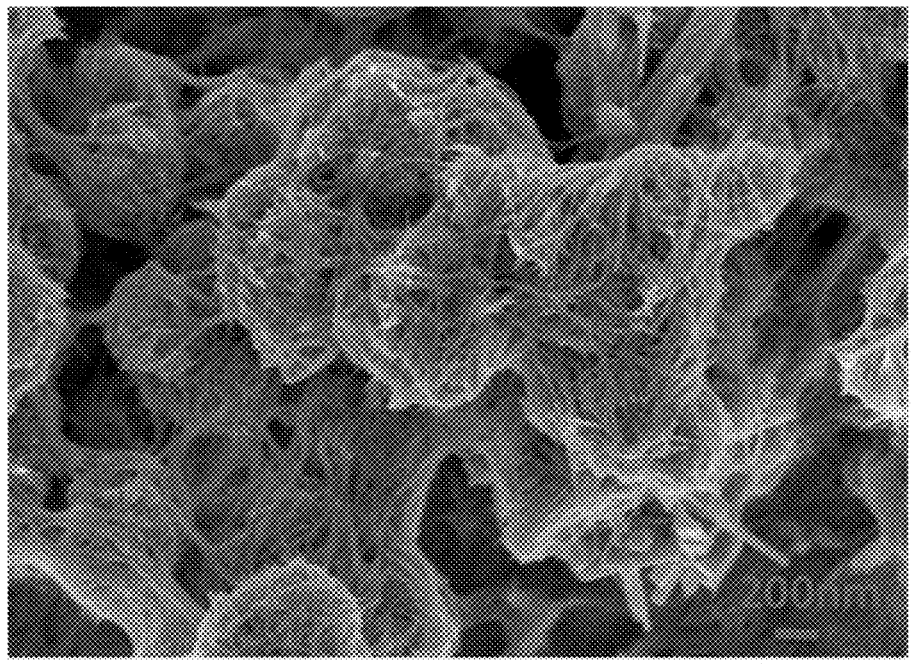
FIG. 5 shows an SEM image of $Na_{0.15}WO_3$.

The surface morphologies of $Na_{0.15}WO_3$ complex were inspected by scanning electron microscopy (SEM), as shown in FIG. 5. The elemental ratio (Na:W) was determined by X-Ray Fluorescence Spectroscopy (XRF).

Figure 6:
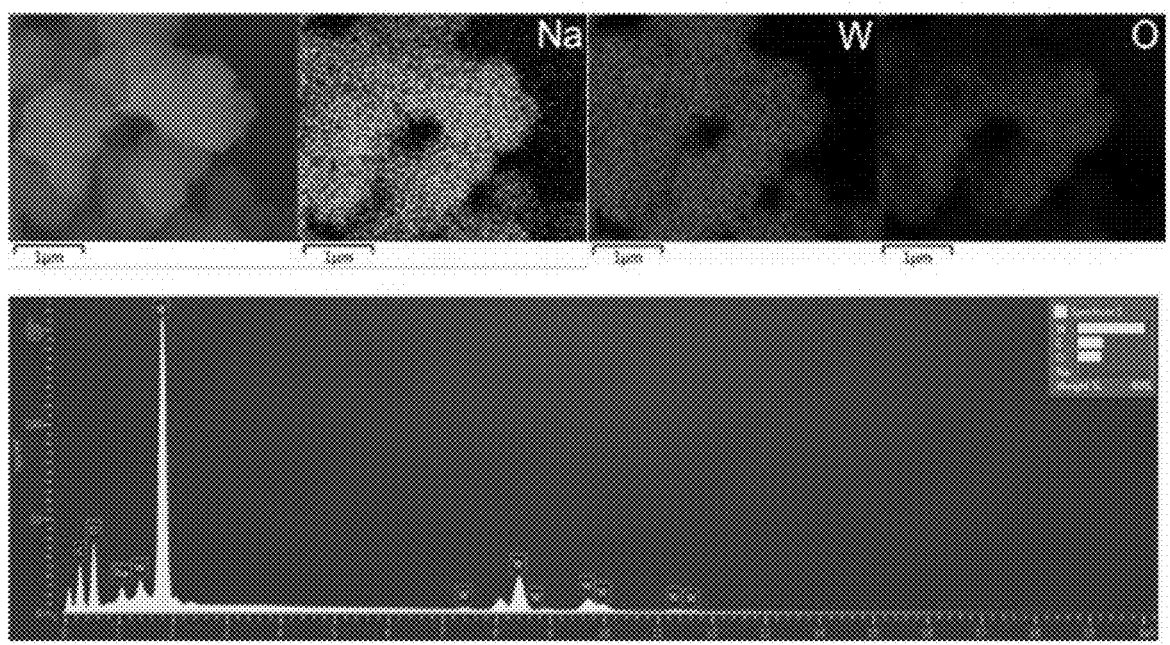
FIG. 6 shows an (a) SEM image and the corresponding EDS mapping images, (b) EDS spectrum of $Na_{0.15}WO_3$.

A typical Energy Dispersive X-ray spectrogram (EDS) spectrum of $Na_{0.15}WO_3$ is shown in FIG. 6b, which confirmed the existence of the elements Na, O, W. The EDS elemental distribution mapping results were presented in FIG. 6a, which confirms the homogeneous distribution of all elements.

Figure 7:
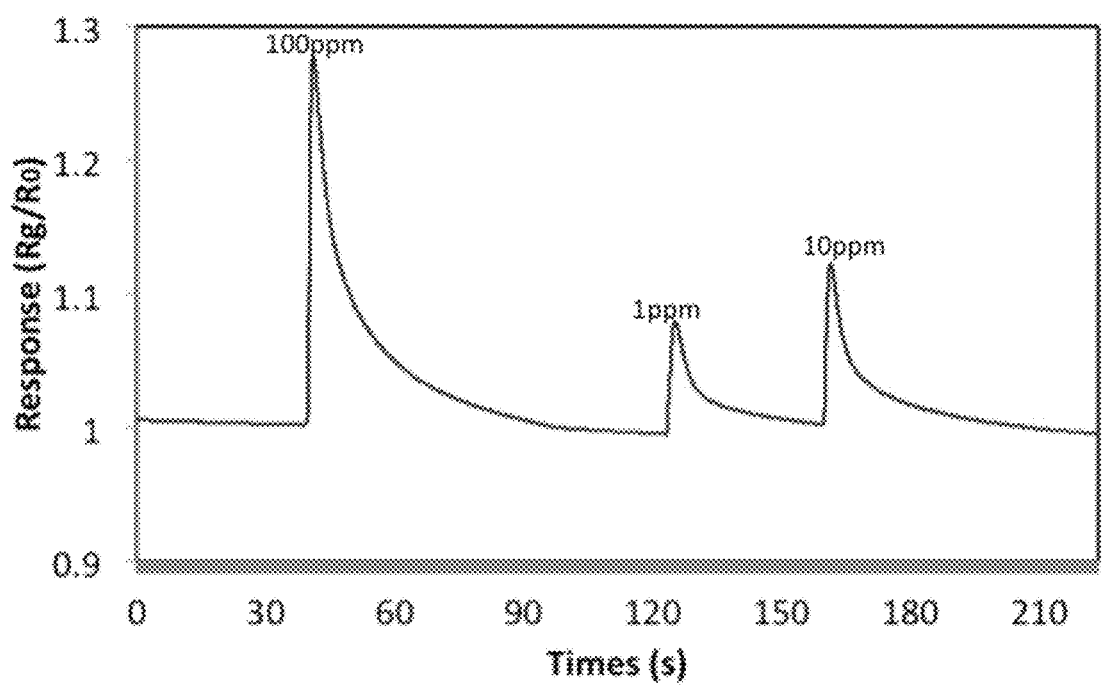
FIG. 7 shows the response curves of the $Na_{0.15}WO_3$ film sensors measured under various acetone gas concentrations.

The response of the sensor was defined as $S=R_g/R_0$, where $R_0$ was the resistance of sensors in air. Rg was the resistance in the presence of the acetone gas. The measurement was performed at room temperature with acetone gas exposure concentration ranging from 1 ppm to 100 ppm, and the test was switched from low concentration to high concentration. A clear increase in the sensor response of $Na_{0.15}WO_3$ was observed with the increasing of gas concentration, as shown in FIG. 7.

Example 3

This example shows an example synthesis method of $Cs_{0.33}WO_3$ and its application for acetone detection at room temperature.

$Cs_{0.33}WO_3$ was synthesized by using a facile hydrothermal treatment of $WCl_6$ solution. In an example synthesis process, 40 mg $WCl_6$ and 1.3 mg Cesium chloride were added into 25 mL of ethanol with ultrasonic for 30 min. And then, the dispersion was transferred into a 50 mL hydrothermal autoclave reactor and was heated at 220° C. for 12 h. Afterward, when the autoclave reactor cooled down to room temperature, the products were obtained by centrifugation at 3000 r/min for 15 min. The pure $Cs_{0.33}WO_3$ powders were finally obtained after being washed with deionized water.

The $Cs_{0.33}WO_3$ sensor was fabricated on a ceramic electrode substrate. A pair of the Au electrode had a thickness of 150 nm. The width and gap were 20 μm and 10 μm, respectively. The sensing film of $Cs_{0.33}WO_3$ was prepared using drop-casting method. The resulting $Cs_{0.33}WO_3$ dispersion was dropped onto the ceramic electrode substrate with a pipette, followed by drying in the oven at 35° C. for 2 h.

Figure 8:
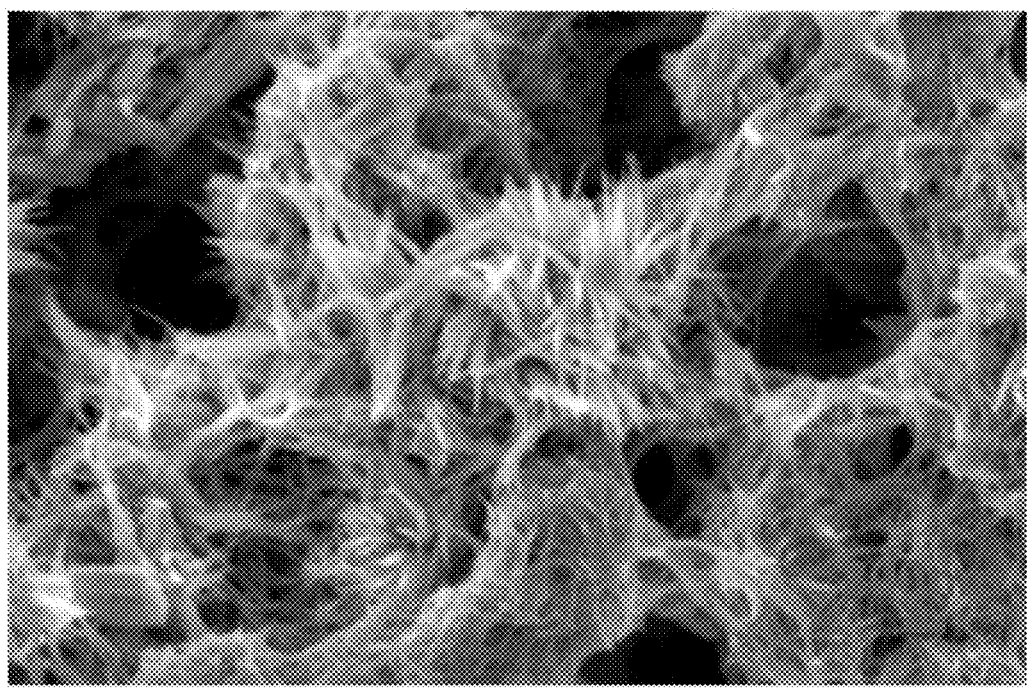
FIG. 8 shows an SEM image of $Cs_{0.33}WO_3$.

The surface morphologies of $Cs_{0.33}WO_3$ complex were inspected by scanning electron microscopy (SEM), as shown in FIG. 8. The elemental ratio (Cs:W) was determined by XRF.

Figure 9:
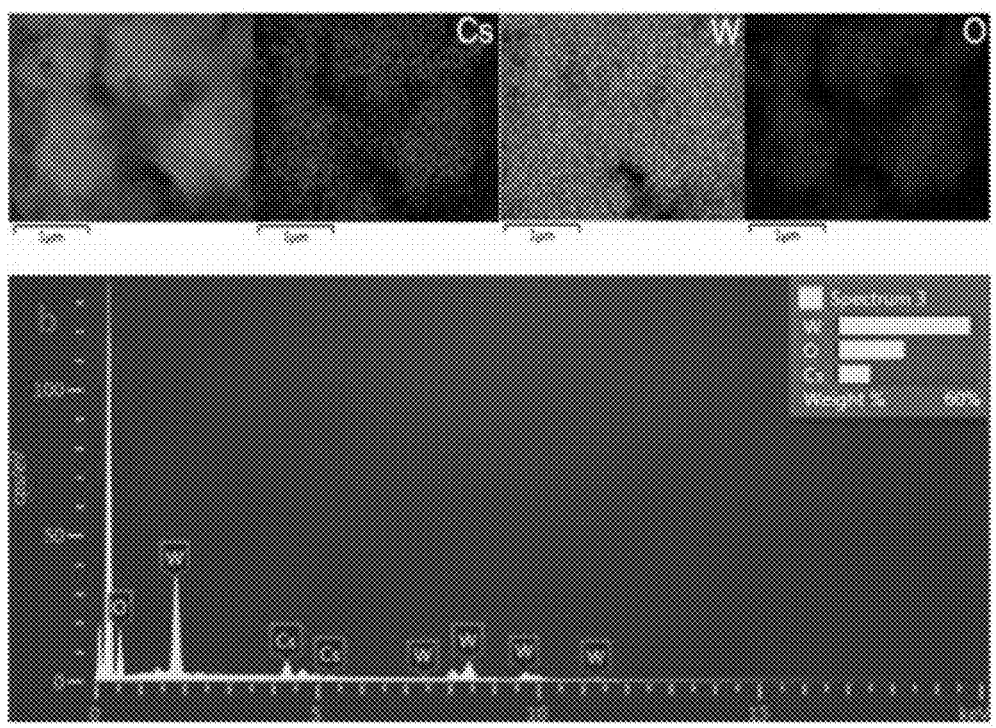
FIG. 9 shows an (a) SEM image and the corresponding EDS mapping images, (b) EDS spectrum of $Cs_{0.33}WO_3$.

A typical Energy Dispersive X-ray spectrogram (EDS) spectrum of $Cs_{0.33}WO_3$ is shown in FIG. 9b, which confirmed the existence of the elements Cs, W and O. The EDS elemental distribution mapping results were presented in FIG. 9a, which confirms the homogeneous distribution of all elements.

Figure 10:
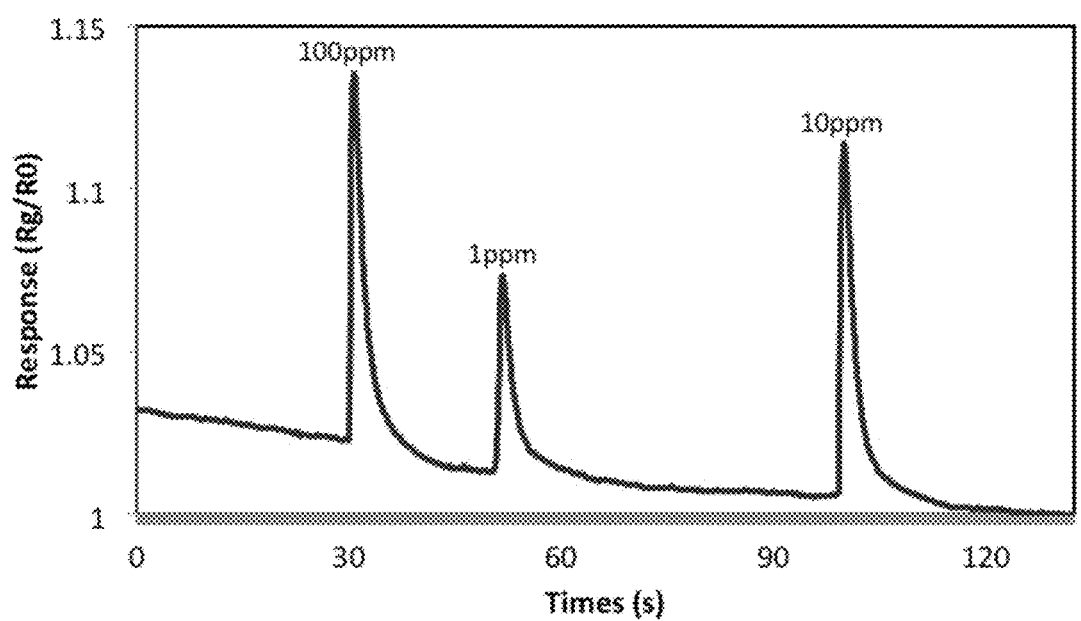
FIG. 10 shows the response curves of the $Cs_{0.33}WO_3$ film sensors measured under various acetone gas concentrations.

The response of the sensor was defined as $S=R_g/R_0$, where $R_0$ was the resistance of sensors in air. $R_g$ was the resistance in the presence of the acetone gas. The measurement was performed at room temperature with acetone gas exposure concentration ranging from 1 ppm to 100 ppm, and the test was switched from low concentration to high concentration. A clear increase in the sensor response of $Cs_{0.33}WO_3$ was observed with the increasing of gas concentration, as shown in FIG. 10.

Example 4

This example shows an example synthesis method of $Na_{0.12}K_{0.2}WO_3$ and its application for acetone detection at room temperature.

$Na_{0.12}K_{0.2}WO_3$ was synthesized using a facile hydrothermal treatment of $WCl_6$ solution. In an example synthesis process, 40 mg $WCl_6$, 1.5 mg sodium chloride, and 1.5 mg potassium chloride were added into 25 mL of ethanol with ultrasonic for 30 min. And then, the dispersion was transferred into a 50 mL hydrothermal autoclave reactor and was heated at 220° C. for 12 h. Afterward, when the autoclave reactor cooled down to room temperature, the products were obtained by centrifugation at 3000 r/min for 15 min. The pure $Na_{0.12}K_{0.2}WO_3$ powders were finally obtained after being washed with deionized water and ethanol for four times.

Figure 11:
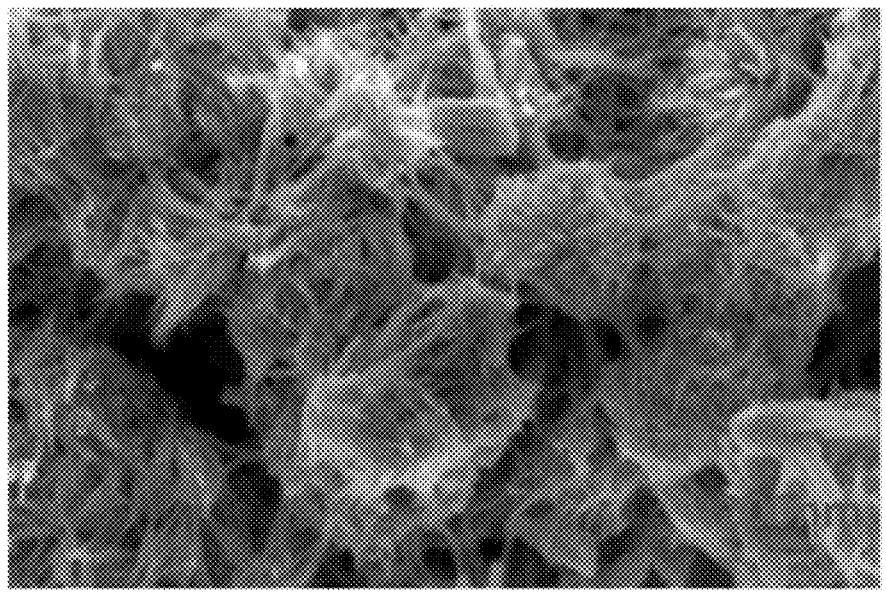
FIG. 11 shows an SEM image of $Na_{0.12}K_{0.2}WO_3$.

The particle morphologies of $Na_{0.12}K_{0.2}WO_3$ complex were inspected by scanning electron microscopy (SEM), as shown in FIG. 11. The material fabricated by this method is in the form of nanorods with ultrathin diameter. The elemental ratio (Na:K:W) was determined by XRF.

Figure 12:
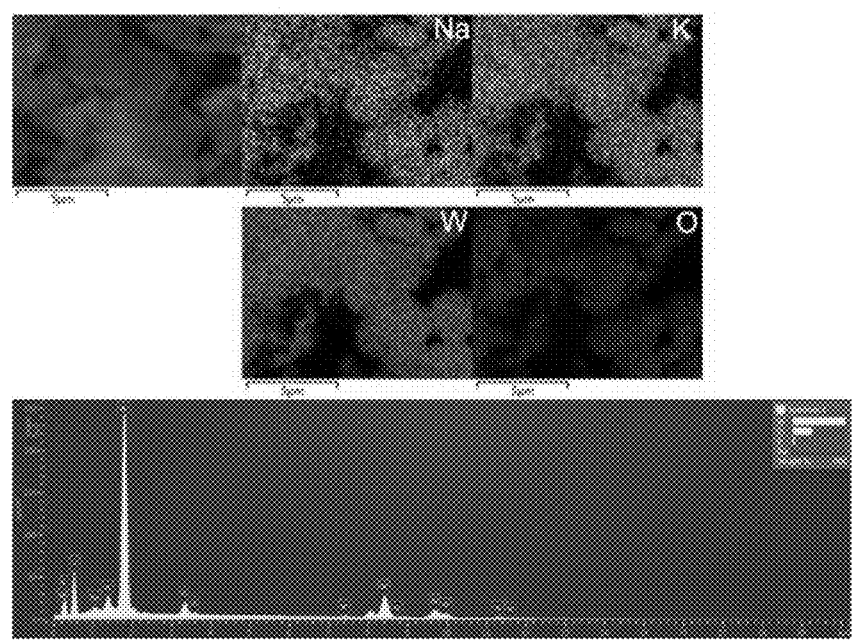
FIG. 12 shows an (a) SEM image and the corresponding EDS mapping images, (b) EDS spectrum of $Na_{0.12}K_{0.2}WO_3$.

A typical Energy Dispersive X-ray spectrogram (EDS) spectrum of $Na_{0.12}K_{0.2}WO_3$ is shown in FIG. 12b, which confirmed the existence of the elements Na, K, O, W. The EDS elemental distribution mapping results were presented in FIG. 12a, which confirms the homogeneous distribution of all elements.

The $Na_{0.12}K_{0.2}WO_3$ sensor was fabricated on a ceramic electrode substrate. A pair of the Pt electrode had a thickness of 150 nm. The width and gap were 20 μm and 10 μm, respectively. The sensing film of $Na_{0.12}K_{0.2}WO_3$ was prepared by using drop-casting method. The resulting $Na_{0.12}K_{0.2}WO_3$ dispersion was dropped onto the ceramic electrode substrate with a pipette, followed by drying in the oven at 35° C. for 2 h.

Figure 13:
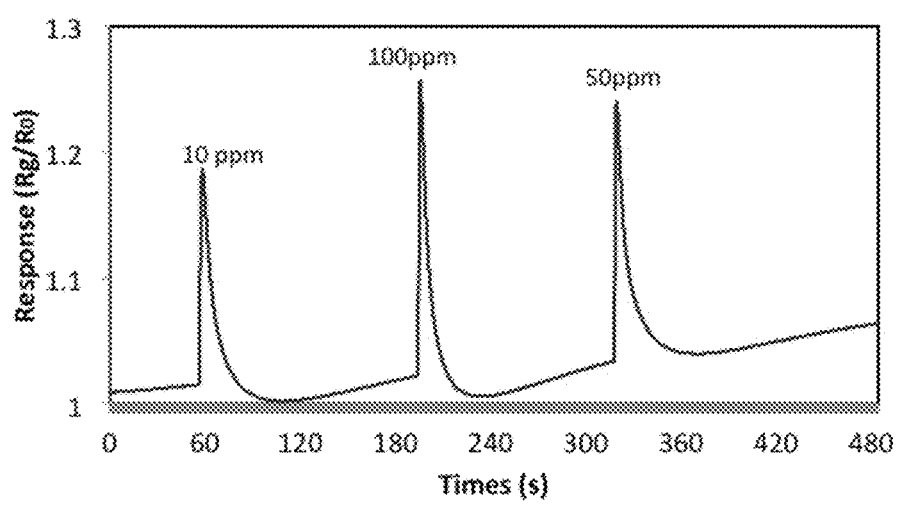
FIG. 13 shows the response curves of the $Na_{0.12}K_{0.2}WO_3$ film sensors measured under various acetone gas concentrations.

The response of the sensor was defined as $S=R_g/R_0$, where $R_0$ was the resistance of sensors in air. $R_g$ was the resistance in the presence of the acetone gas. The measurement was performed at room temperature with acetone gas exposure concentration ranging from 10 ppm to 100 ppm, and the test was switched from low concentration to high concentration. A clear increase in the sensor response of $Na_{0.12}K_{0.2}WO_3$ was observed with the increasing of gas concentration, as shown in FIG. 13.

REFERENCES

[1] Seon-Jin Choi, Inkun Lee, Bong-Hoon Jang, Doo-Young Youn, Won-Hee Ryu, Chong Ook Park, and Il-Doo Kim. Selective Diagnosis of Diabetes Using Pt-Functionalized $WO_3$ Hemitube Networks As a Sensing Layer of Acetone in Exhaled Breath. *Analytical Chemistry.* 2013 85 (3), 1792-1796

[2] Julian King, Alexander Kupferthaler, Birgit Frauscher, Heinz Hackner, Karl Unterkofler, Gerald Teschl, Hartmann Hinterhuber, Anton Amann, Birgit Hogl. Measurement of endogenous acetone and isoprene in exhaled breath during sleep. *Physiol Meas.* 2012 33(3), 413-428.

[3] Toshiaki Funada and Takao Tsuda Tetsuo Ohkuwa, Acetone Response with Exercise Intensity, *Advanced Gas Chromatography—Progress in Agricultural, Biomedical and Industrial Applications.* 2012, ch. 8, 151-160.

[4] R. Xing, Q. Li, L. Xia, J. Song, L. Xu, J. Zhang, Y. Xie, H. Song, Au-modified three-dimensional In2O3 inverse opals: synthesis and improved performance for acetone sensing toward diagnosis of diabetes, *Nanoscale.* 7 (2015) 13051-13060.

[5] A. Staerz, U. Weimar, N. Barsan, Understanding the Potential of $WO_3$ Based Sensors for Breath Analysis, *Sensors.* 16 (2016) 1815.

[6] M. Righettoni, A. Tricoli, S. E. Pratsinis, Si:$WO_3$ Sensors for Highly Selective Detection of Acetone for Easy Diagnosis of Diabetes by Breath Analysis, *Anal. Chem.* 82 (2010) 3581-3587.

[7] S.-J. Choi, B.-H. Jang, S.-J. Lee, B. K. Min, A. Rothschild, I.-D. Kim, Selective Detection of Acetone and Hydrogen Sulfide for the Diagnosis of Diabetes and Halitosis Using $SnO_2$ Nanofibers Functionalized with Reduced Graphene Oxide Nanosheets, *ACS Appl. Mater. Interfaces.* 6 (2014) 2588-2597.

[8] X. Zhou, X. Li, H. Sun, P. Sun, X. Liang, F. Liu, X. Hu, G. Lu, Nanosheet-Assembled $ZnFe_2O_4$ Hollow Microspheres for High-Sensitive Acetone Sensor, *ACS Appl. Mater. Interfaces.* 7 (2015) 15414-15421.

[9] Do Hong Kim, Young-Seok Shim, Jong-Myeong Jeon, Hu Young Jeong, Sung Soo Park, Young-Woon Kim, Jin-Sang Kim, Jong-Heun Lee, and Ho Won Jang. Vertically Ordered Hematite Nanotube Array as an Ultrasensitive and Rapid Response Acetone Sensor. *ACS Applied Materials & Interfaces* 2014 6 (17), 14779-14784

[10] C.-M. Yang, T.-C. Chen, Y.-C. Yang, M.-C. Hsiao, M. Meyyappan, C.-S. Lai, Ultraviolet illumination effect on monolayer graphene-based resistive sensor for acetone detection, *Vacuum.* 140 (2017) 89-95.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A gas sensor comprising: an electrode and a sensing material deposited on the electrode, wherein the sensing material comprises a tungsten bronze, a carbon complex of the tungsten bronze, or a complex of the tungsten bronze with reduced graphene oxide, and the gas sensor has a limit of detection of 100 parts per million (ppm) or less of acetone in a gas sample at an operation temperature of 50° C. or less, wherein the tungsten bronze is $Na_{0.12}K_{0.2}WO_3$.

2. The gas sensor of claim 1, wherein the limit of detection is 50 ppm or less.

3. The gas sensor of claim 1, wherein the electrode has a substrate chosen from ceramic, silica, silicon, glass, a printed circuit board (PCB), or a polyethylene terephthalate (PET) substrate.

4. The gas sensor of claim 1, further comprising a depositing solvent, an adhesive, or both.

5. The gas sensor of claim 1, wherein the sensing material is in a shape of a film.

6. A wearable device comprising the gas sensor of claim 1.

7. The wearable device of claim 6, wherein the wearable device has a volume of 5 $cm^3$ or less.

8. The wearable device of claim 6, wherein the wearable device has a power consumption of 5 μAmp or less.

9. The wearable device of claim 6, wherein the wearable device comprises a shoe, an armband, a sleeve, a jacket, glasses, eye wears, goggles, a glove, a ring, a watch, a wristband, a bracelet, nose ring, ear bud, earphone, an article of clothing, a hat, a headband, a headset, a bra, or jewelry.

10. The wearable device of claim 6, wherein the wearable device is configured to calibrate itself and/or to digitally read concentration of acetone.

11. The wearable device of claim 6, wherein the wearable device is configured to connect with a computer or smartphone that displays metabolic profiles, fat burning status, diet and fitness efficiency, or a combination thereof, in a subject wearing the wearable device.

* * * * *